(12) United States Patent
Notohardjono et al.

(10) Patent No.: US 10,168,303 B2
(45) Date of Patent: Jan. 1, 2019

(54) VIBRATION POWERED ENVIRONMENTAL MONITORING

(71) Applicant: INTERNATIONAL BUSINESS MACHINES CORPORATION, Armonk, NY (US)

(72) Inventors: Budy D. Notohardjono, Poughkeepsie, NY (US); Arkadiy O. Tsfasman, Wappingers Falls, NY (US); John S. Werner, Fishkill, NY (US)

(73) Assignee: International Business Machines Corporation, Armonk, NY (US)

( * ) Notice: Subject to any disclaimer, the term of this patent is extended or adjusted under 35 U.S.C. 154(b) by 63 days.

(21) Appl. No.: 15/364,582

(22) Filed: Nov. 30, 2016

(65) Prior Publication Data

US 2018/0149623 A1 May 31, 2018

(51) Int. Cl.
| | |
|---|---|
| *G01P 15/08* | (2006.01) |
| *G01N 29/22* | (2006.01) |
| *H02N 2/18* | (2006.01) |
| *H02N 1/00* | (2006.01) |
| *H02K 7/18* | (2006.01) |
| *G01K 11/22* | (2006.01) |

(52) U.S. Cl.
CPC ........... *G01N 29/223* (2013.01); *G01K 11/22* (2013.01); *G01P 15/08* (2013.01); *G01P 15/0891* (2013.01); *H02K 7/1892* (2013.01); *H02N 1/00* (2013.01); *H02N 2/181* (2013.01); *H02N 2/186* (2013.01)

(58) Field of Classification Search
CPC .. G01P 15/02; G01P 15/08; G01P 2015/0805; G01P 2015/0825; G01M 99/005; G01N 29/223; H02K 7/1892; H02N 2/186; B81B 3/00; B81B 3/0018; B81B 3/0021; B81B 3/0086

See application file for complete search history.

(56) References Cited

U.S. PATENT DOCUMENTS

| | | | |
|---|---|---|---|
| 6,630,894 B1 | 10/2003 | Boyd et al. | |
| 8,309,942 B2* | 11/2012 | Lal | G01T 1/2018 250/493.1 |
| 8,422,317 B2* | 4/2013 | Kamp | G08B 13/06 365/189.16 |
| 8,766,706 B2 | 7/2014 | Lutz et al. | |

(Continued)

FOREIGN PATENT DOCUMENTS

| | | |
|---|---|---|
| CN | 103036475 A | 4/2013 |
| JP | 2002374661 A | 12/2002 |

(Continued)

OTHER PUBLICATIONS

IBM: List of IBM Patents or Patent Applications Treated as Related (Appendix P), Aug. 17, 2017, pp. 1-2.

(Continued)

*Primary Examiner* — Natalie F Huls
(74) *Attorney, Agent, or Firm* — Dmitry Paskalov

(57) ABSTRACT

A method for monitoring transportation of a package, as well as the apparatus for monitoring transportation, that uses an environmental monitoring device electrically connected to a vibration-to-electricity converter. The vibration-to-electricity converter is electrically attached to the environmental monitoring device.

3 Claims, 4 Drawing Sheets

(56) References Cited

U.S. PATENT DOCUMENTS

| | | | |
|---|---|---|---|
| 9,490,729 B2* | 11/2016 | Hasegawa | H02N 2/188 |
| 2004/0150529 A1 | 8/2004 | Benoit et al. | |
| 2005/0087019 A1 | 4/2005 | Face | |
| 2011/0158806 A1* | 6/2011 | Arms | F03D 1/0658 |
| | | | 416/31 |
| 2013/0106497 A1 | 5/2013 | Lutz et al. | |
| 2015/0229243 A1* | 8/2015 | Chimamkpam | H02N 2/188 |
| | | | 310/323.01 |
| 2016/0099570 A1 | 4/2016 | The' | |
| 2016/0154128 A1 | 6/2016 | Lin et al. | |
| 2016/0196528 A1 | 7/2016 | Lemmon | |
| 2016/0302019 A1 | 10/2016 | Smith et al. | |

FOREIGN PATENT DOCUMENTS

| | | |
|---|---|---|
| JP | 2014062775 A | 4/2014 |
| WO | 2015087537 A1 | 6/2015 |

OTHER PUBLICATIONS

Raunhofer, "Analyzing energy potential," Research News / Feb. 5, 2012, Sensor+Test 2012, Research News, May, 2012, https://www.fraunhofer.de/en/press/research-news/2012/may/analyzing-energy-potential.html, Printed on Oct. 18, 2016, pp. 1-3.

Disclosed Anonymously, "Technique of Cleaning and Charging Cordless Ultrasonic Transducers," An IP.com Prior Art Database Technical Disclosure, IP.com No. IPCOM000225980D, IP.com Electronic Publication Date: Mar. 19, 2013, pp. 1-9.

Wang, "Energy Harvesting for Self-Powered Nanosystems," Nano Res (2008) 1: 1-8, DOI 10.1007/s12274-008-8003-x, School of Materials Science and Engineering, Georgia Institute of Technology, Atlanta, GA, Accepted: May 12, 2008, Copyright Tsinghua Press and Springer-Verlag 2008, pp. 1-8.

Boisseau et al., "Adjustable Nonlinear Springs to Improve Efficiency of Vibration Energy Harvesters," Journal of Applied Mechanics, vol. 80, Issue 6, 2013, Paper No. JAM-12-1470, pp. 1-19.

\* cited by examiner

VIBRATION POWERED ENVIRONMENTAL MONITORING

BACKGROUND

The present invention relates generally to the field of monitoring environment during product shipment, and more particularly to a shipment device that is attached to a package and powered by vibration.

During shipment, a product may experience harmful environmental events that damage the product. For example, the product may experience shock and vibration, extreme temperatures, humidity, and light exposure. The harmful environmental events may damage the product and may be analyzed to improve a product and/or its packaging.

SUMMARY

An embodiment of the invention may include a method for monitoring transportation of a package where a transportation monitoring device is attached to the package. The transportation monitoring device includes an environmental monitoring device electrically attached to a vibration-to-electricity converter. The method may include transporting the package from a first location to a second location. Vibration that occurs during transportation is converted by the vibration-to-electricity converter to an electrical output for use by the environmental monitoring device. The method includes receipt of data from an environmental sensor that is electrically connected to the environmental monitoring device. The method may include recording the received data based on determining that the data from the environmental sensor is above a threshold.

Another embodiment of the invention may include another method for monitoring transportation of a package where the package with a transportation monitoring device is received. The transportation monitoring device includes an environmental monitoring device electrically attached to a vibration-to-electricity converter. The package is received when the package is transported from a first location to a second location, and vibration that occurs during transportation is converted by the vibration-to-electricity converter into electricity for use by the environmental monitoring device. The method includes receiving data from an environmental sensor electrically connected to the environmental monitoring device. The method determines an anomalous event has occurred if a received data from the environmental sensor is above a threshold.

An additional embodiment of the invention may include an apparatus for monitoring transportation of a package that includes an environmental monitoring device electrically connected to a vibration-to-electricity converter. The vibration-to-electricity converter is mechanically attached to the environmental monitoring device with a spring having a spring constant (k). An additional mass attached to the vibration-to-electricity converter creating an oscillating mass (m).

DETAILED DESCRIPTION

Mobile environmental monitoring devices are typically powered by a battery. Battery powered environmental monitoring devices for tracking harmful or anomalous environmental events during shipment may be used only while the power source, such as the battery, produces enough power to operate the equipment. Typically, a fully charged battery can operate a device for the periods that do not exceed 1 week. If the product is shipped between continents, or spend extended periods of time in shipping warehouses (e.g. more than 1 week), the environmental monitoring device would not gather data due to battery exhaustion.

Adding a higher capacity battery or simply adding additional batteries increase the cost of the environmental monitoring device, as well as the size of the device.

According to a present invention, the energy for operating an environmental monitoring device may be generated from vibrations that naturally occur during transportation. Aspects of the present invention, as appreciated by one skilled in the art, may be embodied as a system, method, or computer product. Accordingly, aspects of the present invention may take the form of an embodiment combining software (including firmware, resident software, micro-code, etc.) and hardware aspects which will all generally be referred to as a "module", "method" or "system."

Various aspects of the present invention are described below with reference to flowchart illustrations and/or block diagrams of methods, apparatus (system) and computer program products. Embodiments of the present invention will now be described in detail with reference to the accompanying Figures.

Figure 1:
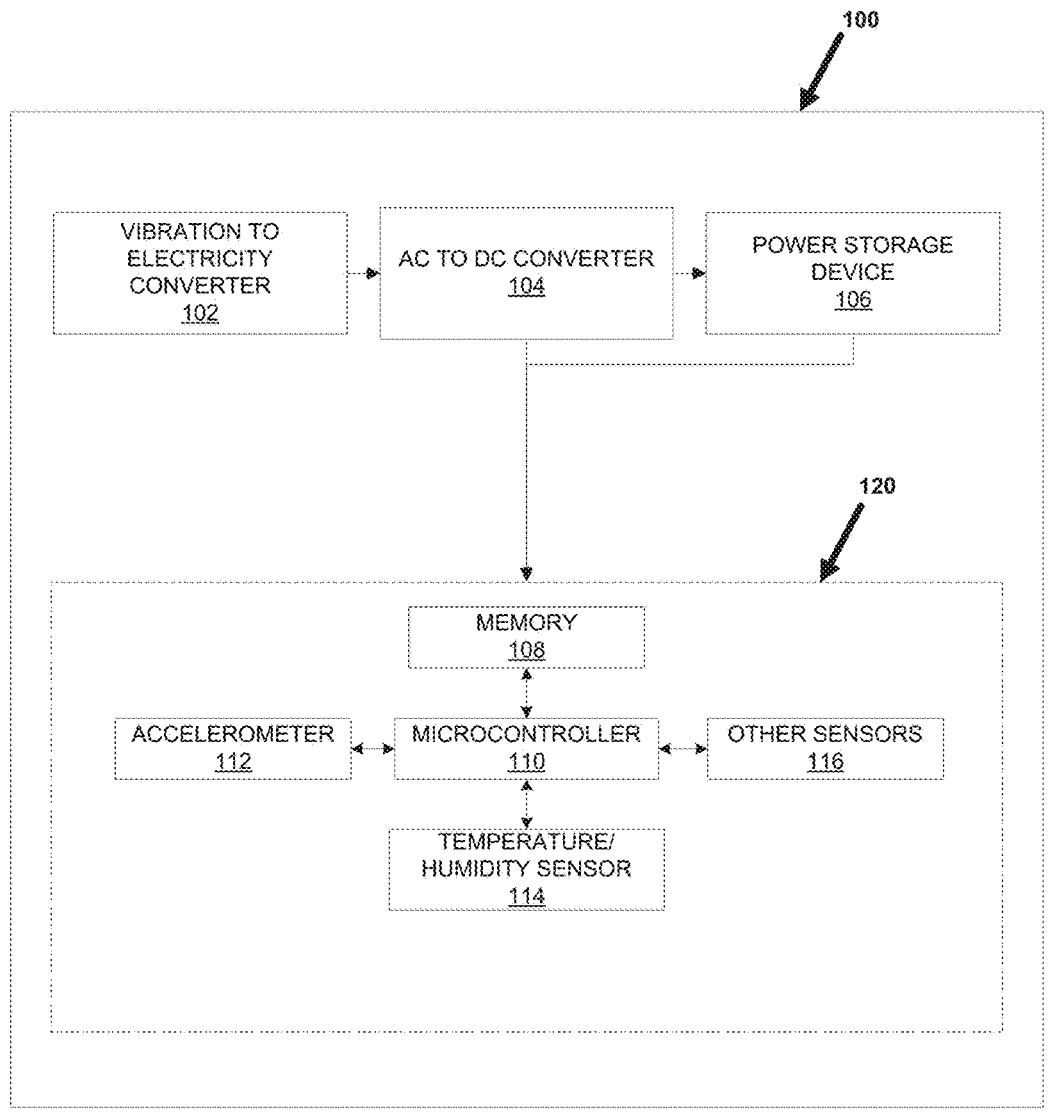
FIG. 1 is a vibration powered environmental monitoring system (VPEMS) 100, in accordance with an embodiment of the present invention.

FIG. 1 is a functional block diagram illustrating a vibration powered environmental monitoring system (VPEMS) 100 where the vibration of VPEMS 100 is used to produce an electrical power to operate an environmental monitoring system, in accordance with an embodiment of the present invention. According to an example embodiment, VPEMS 100 includes a vibration-to-electricity converter 102, AC to DC converter 104, and power storage device 106 (optional) that supply an electrical power to an environmental monitoring system 120. The environmental monitoring system 120 is a device that is configured to collect and record data from various sensors if an environmental condition is above a threshold value. According to an example embodiment, environmental monitoring system 120 includes a microcontroller 110, a memory 108 and various sensors that may measure the environment such as, accelerometer 112, temperature/humidity sensor 114, and other sensors 116. According to an example embodiment, power supply for operations of environmental monitoring system 120 is received from vibration-to-electricity converter 102 which may be optionally coupled with AC to DC converter 104 and power storage device 106.

According to an example embodiment, accelerometer 112 is a device that is configured to measure acceleration such as, for example, vibrations experienced by a product due to being mechanically connected to a machine such as ship, aircraft, automobile, or spaceship. According to an example embodiment, accelerometer 112 is an ultra-low power device that may operate at a low voltage (e.g., 2 volts) and a low current (e.g., 1.8 µA or lower).

According to an example embodiment, temperature/humidity sensor 114 is a multifunctional sensor that is capable of measuring temperature and relative humidity at the same time. According to an example embodiment, temperature/humidity sensor 114 is an ultra-low power device that may operate at a low voltage (e.g., in the range of 2.7 to 5.5 Volts) and low current (e.g., 1.8 µA or lower).

According to an example embodiment, other sensors 116 may be an individual sensor or a set of sensors that are related to a package or a product that is transported. According to an example embodiment, other sensors 116 may be a pressure sensor of ultra-low power configuration that may operate at a low voltage (e.g., 1.62-3.6 volts) and a low current (e.g., 1.3 µA or lower). In other embodiments, other sensors 116 may be a light sensor, a magnetic field sensor, a Geiger counter (radiation sensor) or any other sensors related to the transportation of a product or that may affect or damage the product.

According to an example embodiment, memory 108 provides a data storage where sensors data may be recorded. Memory 108 may be a flash memory that requires a low voltage (e.g., 1.65-3.6 volts) and a low standby current (e.g., 1 µA) to operate.

According to an example embodiment, microcontroller 110 controls the operations of all the components of the environmental monitoring system 120. Microcontroller 110 is designed to receive the measurements from a plurality of sensors and record the data to memory 108 when the measurements are above the predetermined threshold. According to an example embodiment, the functions performed by microcontroller 110 may be programmable via microcode routines according to desired operational characteristics.

According to an optional example embodiment, power storage device 106 is a source of electrical power that stores electrical power for the environmental monitoring system 120. According to an example embodiment, power storage device 106 may be a rechargeable battery or capacitor that may be charged by vibrational energy using vibration-to-electricity converter 102 and AC to DC converter 104. In further embodiments, power storage device 106 may be replaced with other electrical charge storing devices.

According to an example embodiment, AC to DC converter 104 is an electrical circuit capable of transferring an AC current generated by vibration-to-electricity converter 102 to a DC current. AC to DC converter 102 typically includes a rectifier, smoothing capacitance, and a voltage regulator.

According to an example embodiment, vibration-to-electricity converter 102 may be based on a microelectromechanical systems (MEMS) device, capable of converting vibrational energy to electrical energy. MEMS is a technology of microscopic devices, particularly those with moving parts that are made up of components between 1 and 100 micrometers in size. According to an example embodiment, vibration-to-electricity converter 102 may harvest the vibration energy using electrostatic, magnetic induction, or piezoelectric methods. According to an example embodiment, where vibration-to-electricity converter 102 uses an electrostatic method to create electrical energy, whereby an electrical potential is created when the distance between polarized dielectric plates varies due to vibration. In another example embodiment, where vibration-to-electricity converter 102 uses a magnetic induction method to create energy, whereby the vibration creates a varying magnetic field that induces a voltage on a coil that lies in said field. In a further embodiment, where vibration-to-electricity converter 102 uses a piezoelectric method to create energy, a vibration is used as a mechanical stress to a crystal that creates an electrical potential across the sides of the crystal.

Figure 2:
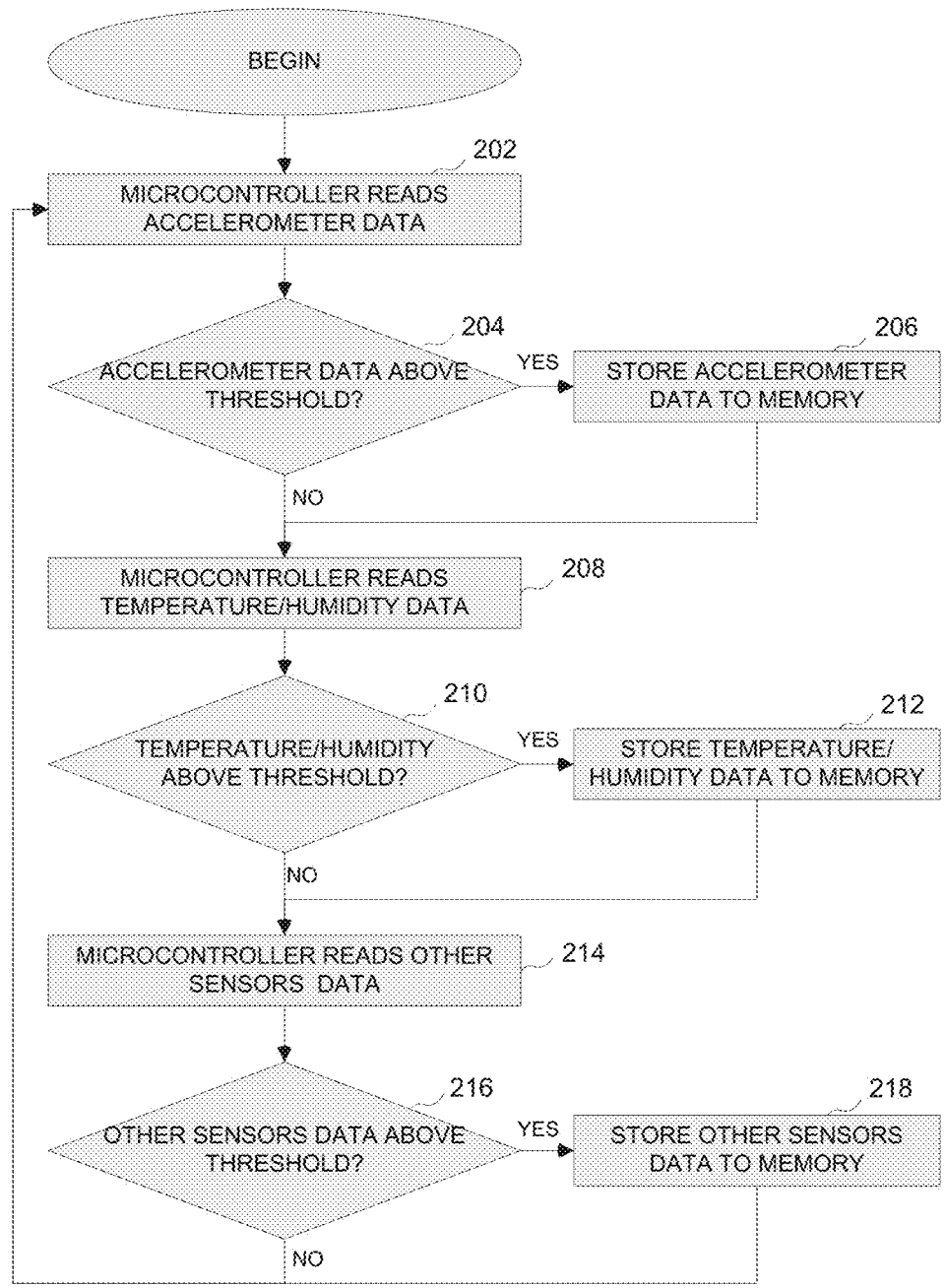
FIG. 2 is a flowchart illustrating an operation of a VPEMS microcontroller, in accordance with an embodiment of the present invention.

FIG. 2 is a flowchart illustrating the operations of microcontroller 110, in accordance with an embodiment of the present invention. Referring to step 202, microcontroller reads accelerometer 112 data. According to an example embodiment, accelerometer 112 measures acceleration in 3 directions and microcontroller calculates the absolute value of the acceleration vector.

Referring to decision 204, microcontroller 110 checks whether accelerometer 112 absolute value is above a threshold value. The threshold value may be pre-determined in accordance with a product requirement, for example for certain fluid transformations the limit may be 2 G. If the absolute value received from accelerometer 112 is above threshold (decision 204, "Yes" branch) microcontroller 110 proceeds to step 206. If the absolute value received from accelerometer 112 is below threshold (decision 204, "No" branch) microcontroller 110 proceeds to step 208.

Referring to step 206, microcontroller 110 stores accelerometer data to memory. According to an example embodiment, microcontroller 110 stores only the absolute value of the acceleration calculated from an acceleration vector. In other embodiment, microcontroller 110 may record 3 values that represent x, y, and z direction acceleration. In further embodiments, microcontroller 110 may record an acceleration data coupled with a corresponding time and date.

Referring to step 208, microcontroller 110 reads temperature/humidity sensor 114 data. According to an example embodiment, temperature/humidity sensor 114 measures a temperature and a relative humidity of the package or a product that is directly attached to VPEMS 100. In other embodiment, temperature/humidity sensor 114 may be connected to the product and transmit the values to microcontroller 110 either wired or wirelessly.

Referring to decision 210, microcontroller 110 checks whether temperature/humidity sensor 114 measures are above threshold values associated with the temperature and humidity values respectively. The threshold values may be pre-determined in accordance with product requirements. If the values received from temperature/humidity sensor 114 are above threshold (decision 210, "Yes" branch) microcontroller 110 proceeds to step 212. If the values received from temperature/humidity sensor 114 are below threshold (decision 210, "No" branch) microcontroller 110 proceeds to step 214.

Referring to step 212, microcontroller 110 stores temperature/humidity sensor 114 data to memory. According to an example embodiment, microcontroller 110 stores only temperature and humidity values that exceed the threshold values. In another embodiment, microcontroller 110 may record the humidity and temperature data coupled with a corresponding time and date.

Referring to step 214, microcontroller 110 reads other sensors 116 data. According to an example embodiment, other sensors 116 data may measure other environmental sensors such as a pressure sensor, a light sensor, a magnetic field sensor, and a radiation sensor.

Referring to decision 216, microcontroller 110 checks whether other sensors 116 measurements are above threshold values associated with the corresponding sensor values. The threshold values may be pre-determined in accordance with product requirements. If the values received from other sensors 116 are above threshold (decision 216, "Yes"

branch) microcontroller 110 proceeds to step 218. If the values received from other sensors 116 are below threshold (decision 216, "No" branch), microcontroller 110 proceeds to step 202.

Referring to step 218, microcontroller 110 stores other sensors 116 data to memory. According to an example embodiment, microcontroller 110 stores only other sensors 116 values that exceed the threshold values. In another embodiment, microcontroller 110 may record other sensors 116 data coupled with a corresponding time and date.

Typically, major transportation methods are shipping the package by trucks, ships and planes. Each of these methods is accompanied by a unique frequency of vibration. Vibration-to-electricity converter 102 may be further improved to harvest an energy in a more efficient way by adding a spring and weight system to take advantage of the unique frequency and to amplify the vibration, when the frequency of the transportation method is known. For example, truck creates a vibration at a frequency of around 30-40 Hz and aircraft vibration frequency is around 100 Hz. Detailed description of improved vibration-to-electricity converter 102 is described in greater detail with regard to FIG. 3.

Figure 3:
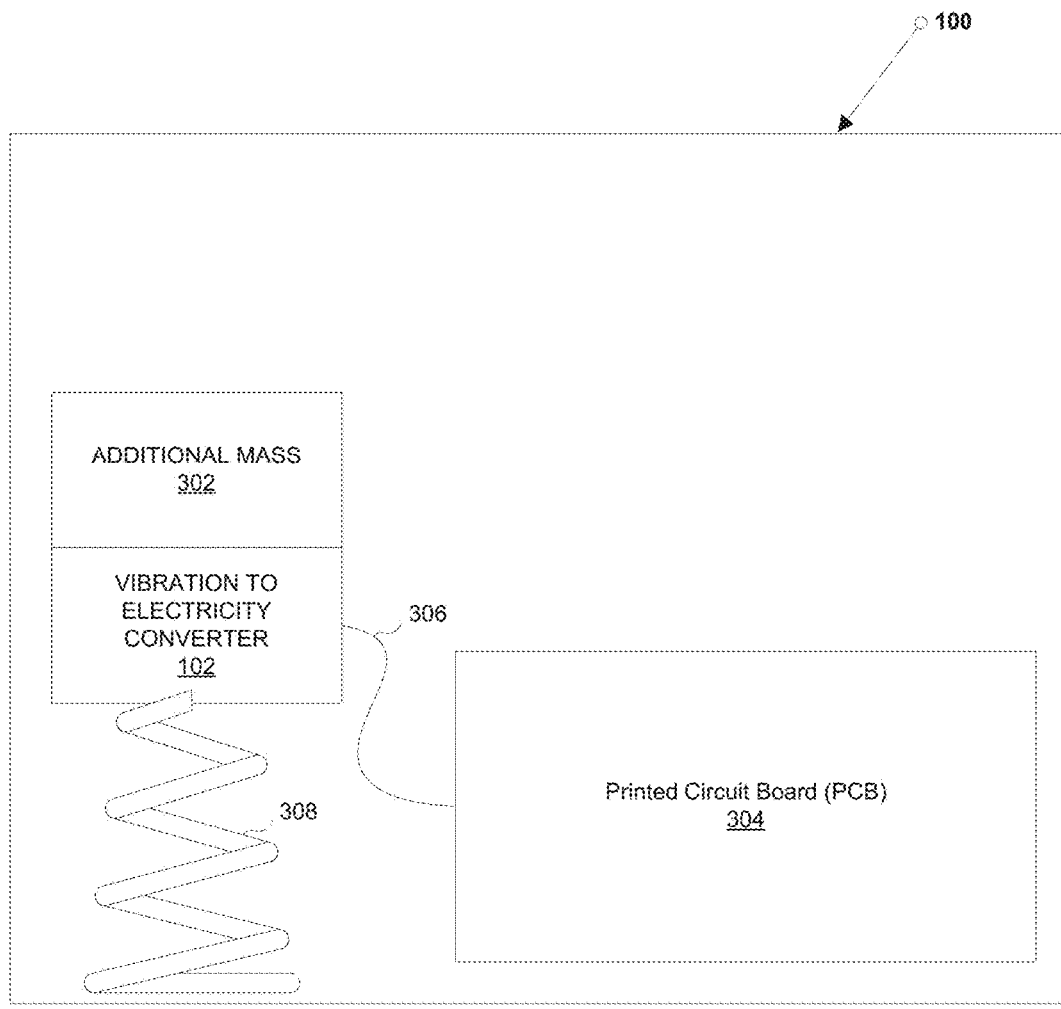
FIG. 3 is a block diagram representing a physical embodiment of an improved VPEMS 100, in accordance with an embodiment of the invention.

FIG. 3 depicts a block diagram representing a physical embodiment of an improved VPEMS 100, in accordance with an embodiment of the invention. According to the example embodiment, VPEMS 100 components except for vibration-to-electricity converter 102 are located on Printed Circuit Board (PCB) 304. PCB 304 is connected by an electrical wire 306 to a vibration-to-electricity converter 102. In another embodiment, PCB 304 may be connected to vibration-to-electricity converter 102 utilizing a wireless transmission device such as near field communication (NFC) or Bluetooth.

As previously mentioned, different transportation vehicles generate different frequencies that may be used to tune the amount of electrical energy produced by the vibration-to-electricity converter 102.

For example, shipping trucks vibrate at around 30-40 Hz and aircrafts at around 100 Hz. By adding additional mass 302 and a corresponding spring 308, more efficient vibration-to-electricity conversion may be accomplished by adjusting additional mass 302 and spring 308 which converts the transportation mediums vibrations to the resonance frequency of vibration-to-electricity converter 102 and amplifies the vibration. It is at this frequency which vibration-to-electricity converter 102 produces the greatest amount of output power. In another embodiment, more than one spring may be attached in xyz orientations, or more than one vibration-to-electricity converters may be attached to different springs to increase the electrical output of the converters.

As the VPEMS 100 vibrates at a first frequency equal to the frequency of the transmission medium ($\omega$), such as a truck, spring 308, connected to an oscillating weight of vibration-to-electricity converter 102 and additional mass 302, resonates at a second frequency ($\omega_0$).

The oscillating weight (that includes additional mass 302 and vibration-to-electricity converter 102) and a spring constant are selected such that the second frequency ($\omega_0$) matches the resonant frequency of the VPEMS 100 keeping the damping ratio ($\zeta$) as low as possible (resulting in a greater g force). In an example embodiment, $\zeta$ should be between 0 and 0.2, more preferably between 0 and 0.1.

Additionally, separating, by mounting separately, vibration-to-electricity converter 102 from PCB 304 decouples the sensors, microprocessor, memory, power storage device, and AC to DC converter on PCB 304 from the tuned frequency used by the vibration-to-electricity converter 102 preventing excess vibrations to the other components.

The required oscillating weight (m) and spring constant (k) may be calculated using a driven damped harmonic oscillator equation $$m\frac{d^2x}{dt^2} + c\frac{dx}{dt} + kx = f(t),$$

where x represents displacement and c represents the dampening coefficient of the spring with the oscillating weight. f(t) is the external dynamic force applied to the vibration-to-electricity converter (function representing the vibrations of the transmission medium). For example, if the transmission mediums vibrations can be represented by a sinusoidal driving force $f(t)=F_0 \sin(\omega t)$, the steady state solution to the driven damped harmonic oscillator equation would be $$x(t) = \frac{F_0}{mZ_m\omega}\sin(\omega t + \varphi), \text{ with } Z_m = \sqrt{(2\omega_0\zeta)^2 + \frac{1}{\omega^2}(\omega_0^2 - \omega^2)} \text{ and}$$

$$\varphi = \arctan\left(\frac{2\omega\omega_0\zeta}{\omega^2 - \omega_0^2}\right).$$

Additionally, the mass (m) and spring constant (k) may then be chosen to minimize damping ratio $$\left(\zeta = \frac{c}{2\sqrt{mk}}\right)$$

to satisfy the steady state solution, where (c) is a dampening coefficient that is a property of a spring material and geometry (c may be calculated using the equation $c^2-4km<0$). Satisfying this equation means that the system is underdamped which leads to more oscillations and hence, a higher power output from vibration-to-electricity converter 102.

The second frequency may be calculated using resonant frequency equation $\omega_r = \omega_0\sqrt{1-\zeta^2}$ where damping ratio $\zeta$ should be as low as possible. As previously mentioned, $\zeta$ should be between 0 and 0.2, more preferably between 0 and 0.1.

Figure 4:
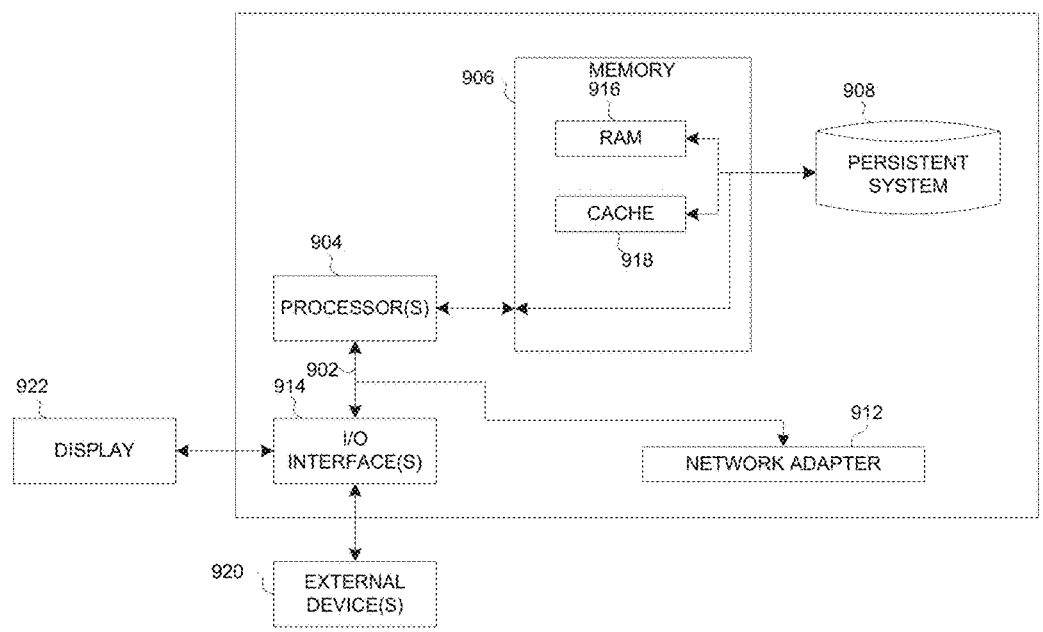
FIG. 4 is a block diagram depicting the example embodiment of hardware components of, microcontroller 110, in accordance with an embodiment of the invention.

FIG. 4 depicts a block diagram of components, such as microcontroller 110 in accordance with an illustrative embodiment of the present invention. It should be appreciated that FIG. 4 provides only an illustration of one implementation and does not imply any limitations with regard to the environments in which different embodiments may be implemented. Many modifications to the depicted environment may be made.

A microcontroller 110 includes communications fabric 902, which provides communications between computer processor(s) 904, memory 906, persistent storage 908, communications unit 912, and input/output (I/O) interface(s) 914. Communications fabric 902 can be implemented with any architecture designed for passing data and/or control information between processors (such as microprocessors, communications and network processors, etc.), system memory, peripheral devices, and any other hardware components within a system. For example, communications fabric 902 can be implemented with one or more buses.

Memory 906 and persistent storage 908 are computer-readable storage media. In this embodiment, memory 906 includes random access memory (RAM) 916 and cache memory 918. In general, memory 906 can include any suitable volatile or non-volatile computer-readable storage media.

A microcontroller 110 program is stored in persistent storage 908 for execution by one or more of the respective computer processors 904 via one or more memories of memory 906. In this embodiment, persistent storage 908 includes a magnetic hard disk drive. Alternatively, or in addition to a magnetic hard disk drive, persistent storage 908 can include a solid state hard drive, a semiconductor storage device, read-only memory (ROM), erasable programmable read-only memory (EPROM), flash memory, or any other computer-readable storage media that is capable of storing program instructions or digital information.

The media used by persistent storage 908 may also be removable. For example, a removable hard drive may be used for persistent storage 908. Other examples include optical and magnetic disks, thumb drives, and smart cards that are inserted into a drive for transfer onto another computer-readable storage medium that is also part of persistent storage 908.

Communications unit 912, in these examples, provides for communications with other data processing systems or devices. In these examples, communications unit 912 includes one or more network interface cards. Communications unit 912 may provide communications through the use of either or both physical and wireless communications links. TVP may be downloaded to persistent storage 908 through communications unit 912.

I/O interface(s) 914 allows for input and output of data with other devices that may be connected to microcontroller 110. For example, I/O interface 914 may provide a connection to external devices 920 such as a keyboard, keypad, a touch screen, and/or some other suitable input device. External devices 920 can also include portable computer-readable storage media such as, for example, thumb drives, portable optical or magnetic disks, and memory cards. Software and data used to practice embodiments of the present invention, e.g., microcontroller 110 may be stored on such portable computer-readable storage media and can be loaded onto persistent storage 908 via I/O interface(s) 914. I/O interface(s) 914 can also connect to a display 922.

Display 922 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, a computer-readable storage device, tangible storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. An apparatus for monitoring transportation of a package, the apparatus comprising:
    an environmental monitoring device electrically connected to a vibration-to-electricity converter, wherein the vibration-to-electricity converter is a microelectromechanical system (MEMS) mechanically attached to the environmental monitoring device with a spring having a spring constant (k); and
    an additional mass attached to the vibration-to-electricity converter creating an oscillating mass (m).

2. The apparatus of claim 1 wherein the MEMS is selected from a group consisting of: a piezoelectric vibration-to-electricity converter, a magnetic induction vibration-to-electricity converter or electrostatic vibration-to-electricity converter.

3. The apparatus of claim 1 wherein the oscillating mass (m) and the spring constant (k) are selected by satisfying an equation $$m\frac{d^2x}{dt^2} + c\frac{dx}{dt} + kx = f(t)$$

where x is a spring displacement, c is a dampening coefficient of the spring, and f(t) is an external dynamic force applied to the vibration-to-electricity converter.

* * * * *